(12) United States Patent
Chen et al.

(10) Patent No.: US 7,023,955 B2
(45) Date of Patent: Apr. 4, 2006

(54) X-RAY FLUORESCENCE SYSTEM WITH APERTURED MASK FOR ANALYZING PATTERNED SURFACES

(75) Inventors: Zewu Chen, Schenectady, NY (US); Shinichi Terada, Uji Kyoto (JP)

(73) Assignee: X-Ray Optical System, Inc., East Greenbush, NY (US)

( * ) Notice: Subject to any disclaimer, the term of this patent is extended or adjusted under 35 U.S.C. 154(b) by 210 days.

(21) Appl. No.: 10/639,359

(22) Filed: Aug. 12, 2003

(65) Prior Publication Data

US 2005/0036583 A1  Feb. 17, 2005

(51) Int. Cl.
*G01N 23/223* (2006.01)

(52) U.S. Cl. .......................... 378/44; 378/147

(58) Field of Classification Search ................ 378/34, 378/35, 44, 45, 46, 49, 50, 145, 147; 250/505.1
See application file for complete search history.

(56) References Cited

U.S. PATENT DOCUMENTS

| | | | | |
|---|---|---|---|---|
| 4,797,906 A | | 1/1989 | Smith ........................... 378/44 |
| 5,175,755 A | | 12/1992 | Kumakhov .................. 378/34 |
| 5,192,869 A | | 3/1993 | Kumakhov .............. 250/505.1 |
| 5,299,252 A | * | 3/1994 | Takahashi .................... 378/50 |
| 5,497,008 A | | 3/1996 | Kumakhov .............. 250/505.1 |
| 5,570,408 A | | 10/1996 | Gibson ...................... 378/145 |
| 5,604,353 A | | 2/1997 | Gibson et al. ........... 250/505.1 |
| 5,686,314 A | * | 11/1997 | Miyazaki ................... 436/177 |
| 6,381,303 B1 | | 4/2002 | Vu et al. ...................... 378/46 |
| 2003/0142781 A1 | | 7/2003 | Kawahara et al. ............ 378/44 |

FOREIGN PATENT DOCUMENTS

| | | |
|---|---|---|
| EP | 1 102 061 A1 | 5/2001 |
| JP | 63-151843 | 6/1988 |
| JP | 01-118757 | 5/1989 |
| JP | 03-087640 | 4/1991 |
| JP | 04-372845 | 12/1992 |
| JP | 2002-250704 | 9/2002 |

* cited by examiner

*Primary Examiner*—Edward J. Glick
*Assistant Examiner*—Courtney Thomas
(74) *Attorney, Agent, or Firm*—Jeffrey R. KLembczyk, Esq.; Kevin P. Radigan, Esq.; Heslin Rothenberg Farley & Mesiti, P.C.

(57) ABSTRACT

Measurement technique and apparatus for examining a region of a patterned surface such as an integrated circuit (IC). Excitation x-ray, neutron, particle-beam or gamma ray radiation is directed toward a two-dimensional sample area of the IC. Emissions (e.g., x-ray fluorescence—XRF) from the sample area are detected. A mask is placed in a planar radiation path formed by the source, detector and the sample area, and in one embodiment moveable relative to the sample area. The mask includes an elongate aperture to substantially confine the excitation radiation directed to the sample area, and the emissions from the sample area, to the planar radiation path when arranged parallel to a first axis of the two-dimensional sample area. The invention allows predictive measurement of feature characteristics in active circuit regions of the IC, using sample areas outside of these regions.

46 Claims, 9 Drawing Sheets

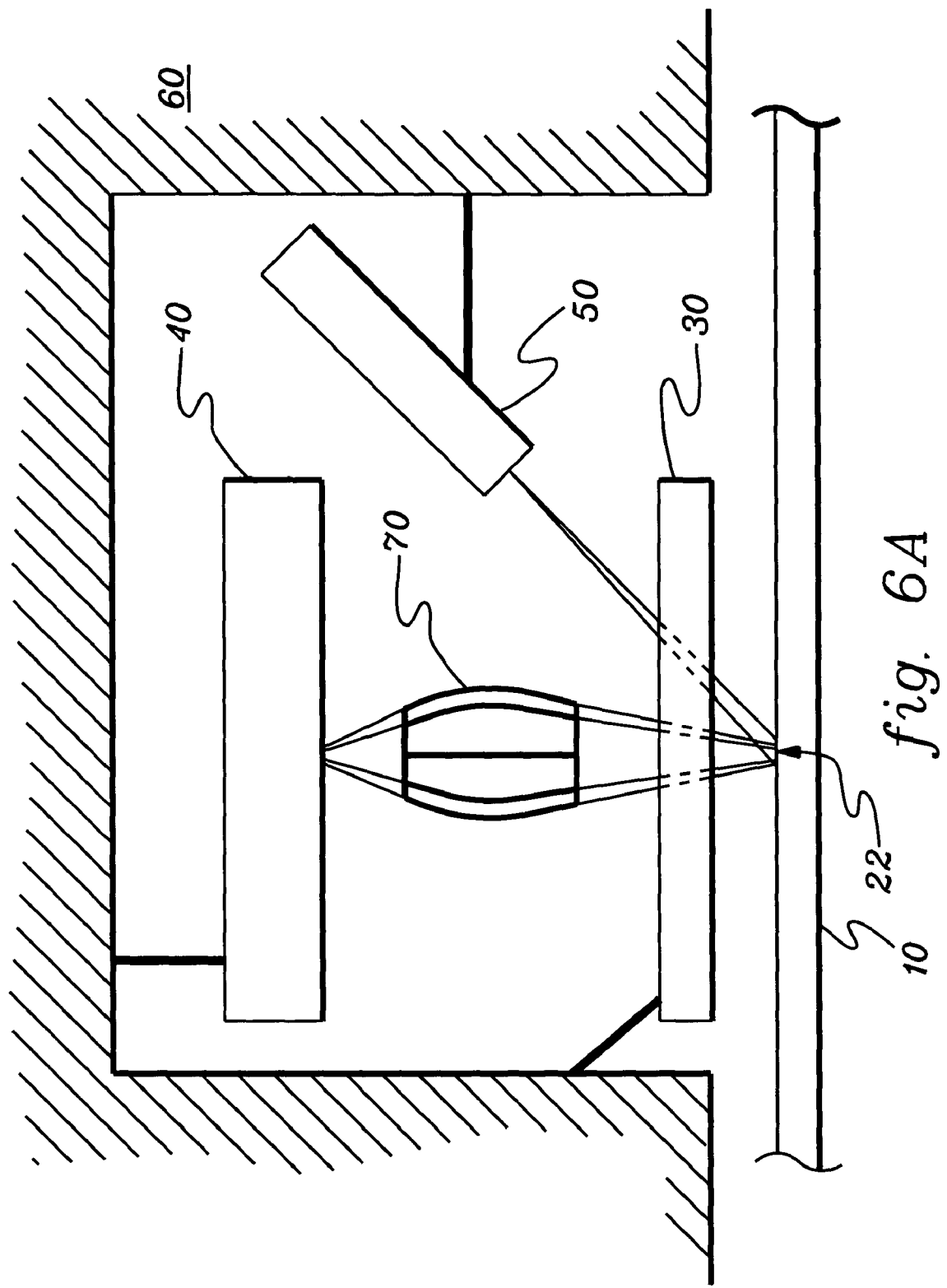

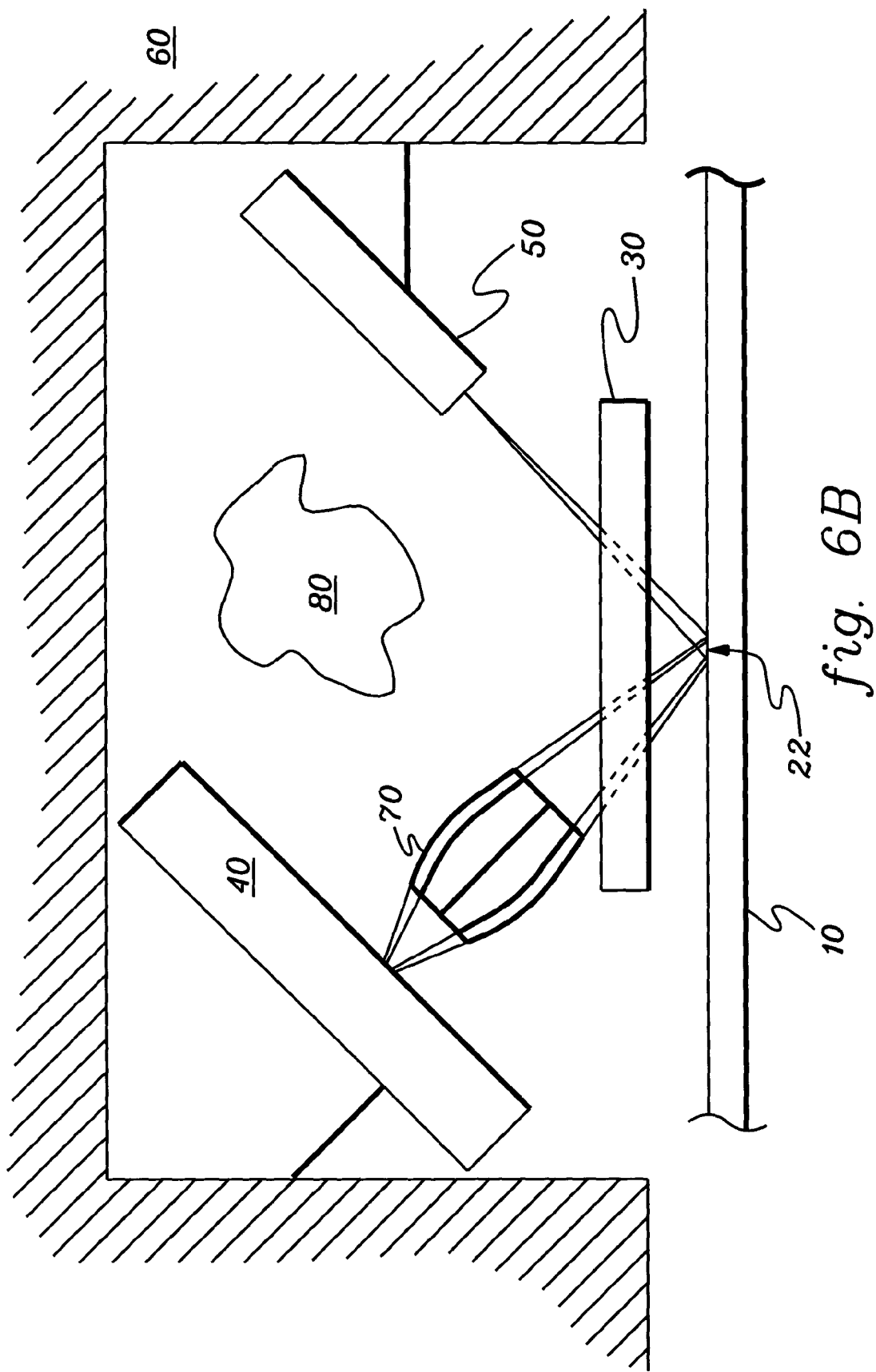

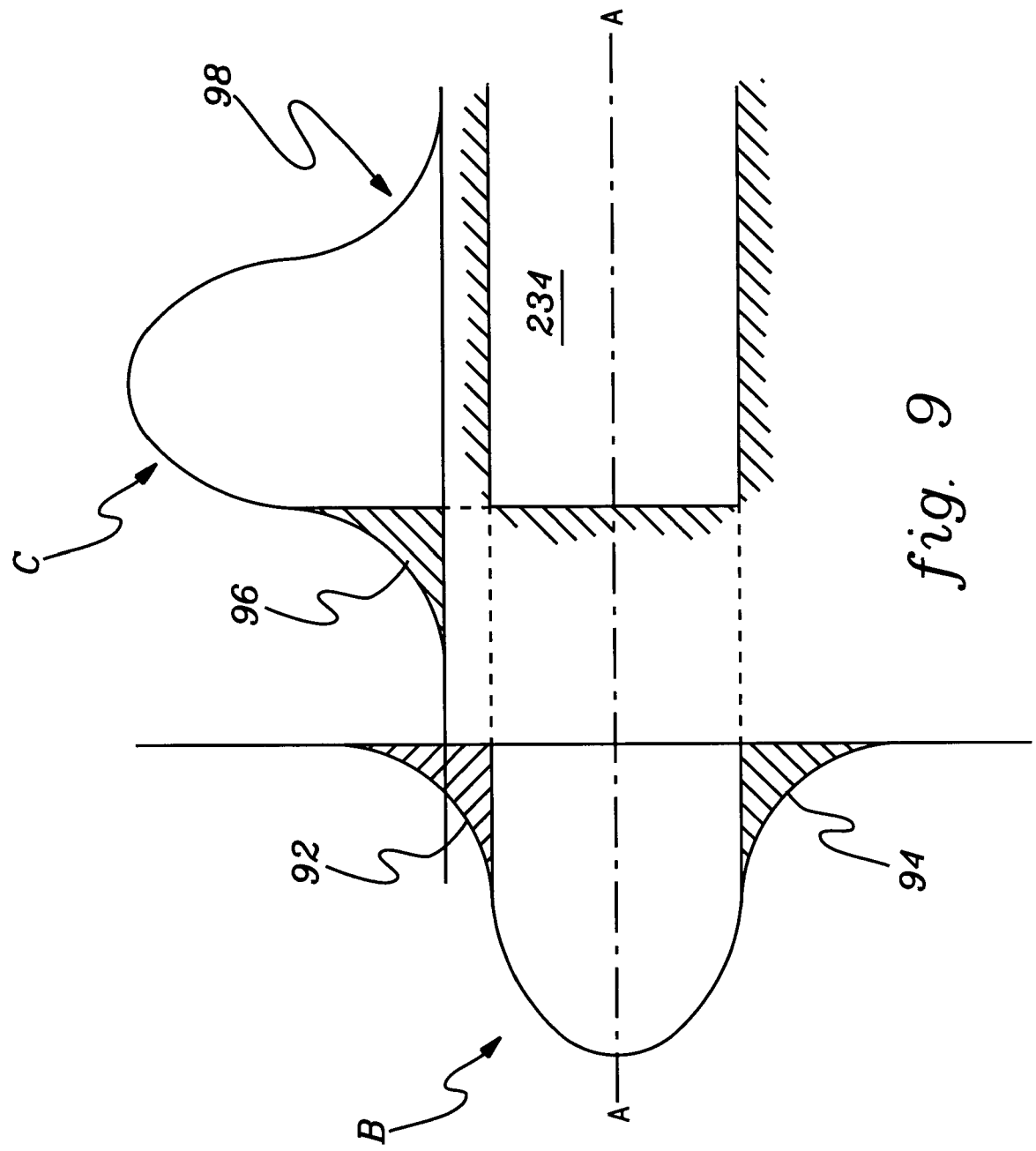

X-RAY FLUORESCENCE SYSTEM WITH APERTURED MASK FOR ANALYZING PATTERNED SURFACES

GOVERNMENT RIGHTS STATEMENT

This invention was made with Government support under Contract #: DMI-0091570 awarded by the National Science Foundation to X-Ray Optical Systems, Inc. The Government has certain rights in this invention.

TECHNICAL FIELD

The present invention relates to analytical instruments. More particularly, the present invention relates to an apparatus and technique for controlling an x-ray beam exciting a sample, and the resultant fluorescence emitted from the sample, to improve analysis results. The invention is particularly suited to x-ray fluorescence (XRF) measurement of patterned surfaces such as small regions of materials forming semiconductor integrated circuits.

BACKGROUND OF THE INVENTION

X-ray fluorescence (XRF) analysis is universally recognized as a very accurate method of measuring the atomic composition and other characteristics of a sample material. This technique (and its close relatives) involve irradiating a sample area with high energy radiation, such as x-rays, gamma rays, neutrons or particle beams and observing the resulting fluorescence emitted by the sample area.

As discussed further below, certain challenges exist in applying XRF techniques to patterned surfaces having many, closely spaced heterogeneous materials—for example, semiconductor integrated circuits (ICs), flat panel displays, surface acoustic wave (SAW) devices, printed circuit boards, planar lightwave circuits, etc. During IC fabrication, many complicated processes are used to deposit and pattern many differing materials on a wafer. XRF can assist in monitoring certain material characteristics, for example, the thickness of deposited films. However, the extremely small feature sizes in chip regions of the IC are difficult to measure directly with XRF. XRF systems have excitation beam sizes much larger than certain feature sizes in use now, and those planned for the future. The present invention is directed to improved systems and techniques which overcome these challenges and apply the power and accuracy of XRF measurements to these applications.

XRF systems generally include a source of excitation radiation, an optic for directing the radiation toward a sample, a radiation detector to detect the stimulated fluorescence emissions from the sample (possibly through another optic), and a display of the spectral output. As the excitation photons strike the sample, they knock electrons out of their orbits around the nuclei of the atoms in the sample, creating vacancies that destabilize the atoms. The atoms stabilize when electrons from the outer orbits are transferred to the inner orbits. These atoms emit a characteristic x-ray fluorescence photon representing the difference between the two binding energies of the corresponding orbits. The detector collects this spectrum of photons and converts them to electrical impulses proportional to the energies of the various x-rays in the sample's spectrum. Since each element has a different and identifiable x-ray fluorescence signature, an operator can determine the presence and concentration of the element(s) within the sample by reviewing specific areas of the emitted spectrum.

The excitation spectra can be intentionally narrowed to a specific, "monochromatic" range. This will lower background noise from adjacent radiation bands, enabling a particular concentration of a known material to be measured. For example, the thickness of a layer of known material can be determined with monochromatic radiation tuned to the material's known fluorescence spectrum. This is accomplished, for example, using monochromating optical element(s) in the excitation path.

Patterned surfaces such as integrated circuits (ICs), flat panel displays, surface acoustic wave (SAW) devices, printed circuit boards, planar lightwave circuits, etc. present special analysis challenges because they include many layers of different materials. IC materials include the semiconductors themselves (e.g., silicon), the various insulating layers (e.g., oxides) and the metallic materials forming electrical interconnect lines or barrier layers (e.g., titanium or tantalum films). Feature characteristics, i.e., the thickness of a metallic film, can be measured using XRF techniques. And because the small feature sizes of IC features require great precision of the various processes used (deposition, etching, implantation, etc.), XRF measurements also enable accurate monitoring of these processes.

Accurate XRF techniques in these applications generally require a constant x-ray flux on the sample line itself, and detection of fluorescence attributable only to a calibrated line width of sample material. Flux directed toward other lines, and the resultant fluorescence emitted from those lines, may confuse the results. Alternatively, if other sample regions must fall in the beam footprint, the consolidated "coverage ratio" of all such regions should be constant and calibrated into the system—necessitating very accurate alignment and movement during measurement. In the IC chip regions, however, many different materials of small sizes are spaced by very small distances. This will affect the accuracy of an XRF measurement directed to a particular sample material. For example, interconnect lines or barrier layers can have sub-micron line widths in the chip regions. These widths will only decrease with time and advances in technology. It is difficult to narrow an x-ray beam to such widths, without stimulating other adjacent regions and confusing the XRF results. Alternatively, if the system is calibrated to a certain coverage ratio of sample material in the beam footprint for narrower lines, careful alignment and movement is required of the system during measurement to maintain the coverage ratio, and thus the integrity of the calibrated and measured values. Therefore, it is important to closely control the excitation beam spot size, and also to collect most if not all of the fluorescence emitted from the sample material itself for accurate XRF results.

Certain techniques may improve analysis of films deposited during IC fabrication. For example, sacrificial test wafers can be used. The film material can be deposited over large areas—with no other materials near an XRF sample area. Comparatively large sample areas can therefore be made available for XRF measurements of film thickness. However, this technique assumes that measurements made on the test wafer will "predict" the dimensions of the film deposited over the final wafer. Considering all of the variables in IC deposition and etch processes, this may not be a valid assumption. Moreover, this technique incurs the time and expense of processing an extra test wafer.

Therefore, improved techniques are required for analysis of small, patterned features, while exploiting the benefits of well-known measurement techniques (e.g., XRF) normally used for larger sample areas in other applications.

SUMMARY OF THE INVENTION

The shortcomings of the prior art are overcome, and additional advantages are provided, by the disclosed technique and apparatus for examining a region of a patterned surface. Excitation x-ray, neutron, particle-beam or gamma ray radiation is directed toward a two-dimensional sample area of the IC. Emissions (e.g., fluorescence) from the sample area are detected. A mask is placed in a planar radiation path formed by the source, detector and the sample area, and moveable relative to the sample area. The mask includes an elongate aperture to substantially confine the excitation radiation directed to the sample area, and the emissions from the sample area, to the planar radiation path when arranged parallel to a first axis of the two-dimensional sample area.

The mask, source, and detector can be moved relative to the IC, to allow analysis of any desired regions in one embodiment; and in another embodiment the mask may be fixed (e.g., a contact mask).

An additional optical element can be used for controlling the excitation radiation from the source, through the elongate aperture, and toward the two-dimensional sample area of the IC. An optical element can also be used for directing the emissions from the aperture to the detector. The optical element can be, for example, a monocapillary element, a polycapillary element, a curved crystal element, a multilayer element, a pin-hole element or a slot element. The optical element may provide beam gain and beam control.

The excitation radiation can be substantially monochromatic in a radiation band characteristic of a sample material, using a monochromating optical element.

The width of the elongate aperture of the mask is sized according to the dimension of the sample area measured along a second axis perpendicular to the first axis of the sample area. In one embodiment, the subject region of the IC is a scribe-line region between chip regions of the IC. The scribe-line region includes the sample area which has a uniform layer of sample material. The uniform layer of sample material in the sample area corresponds to material used for substantially smaller features in the chip regions of the IC. Measuring a characteristic in this scribe line region (e.g., film thickness) can be a valuable and accurate predictor of the thickness of the highly patterned features in the chip region, which cannot be as easily measured using XRF because of their small size.

Further features and advantages are realized by the systems and techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed at the conclusion of the specification. The foregoing and other objects, features, and advantages of the invention are apparent from the following detailed description, taken with the accompanying drawings in which:

FIGS. 6a–b are side, sectional views of a spectroscopy system showing arrangements of a radiation source, focusing optic, mask and detector according to alternate, exemplary embodiments of the present invention;

FIG. 9 is a top view of one embodiment of a mask of the present invention with beam profile plots superimposed showing the stopping action of the mask.

BEST MODE FOR CARRYING OUT THE INVENTION

An apparatus and associated analytical techniques are disclosed for effectively analyzing certain regions of patterned surfaces, while preventing other areas of the surface and undesireable beam scattering from negatively impacting the results. This technique is especially useful for analyzing test regions in the scribe lines between chip regions of an integrated circuit, using x-ray or other related equipment having certain minimal space and sample area requirements.

As discussed above, the small feature sizes currently forming patterned surfaces such as semiconductor ICs present certain analysis challenges. X-ray fluorescence (XRF), x-ray diffraction (XRD), and x-ray reflectivity (XRR) systems involve the use of radiation sources, optics, detectors which can be difficult to accurately place over sub-micron sample areas. Moreover, the excitation beam spot sizes, though dramatically improved to the 10 micron range in the last few years, are still larger than the IC feature sizes now in use, and those planned for the "nanosystems" of the future.

Sample materials (e.g., specialty films) are usually deposited over an IC wafer, and then patterned (e.g., etched) according to sacrificial masks to form the IC device structures and interconnect lines. The remaining patterned layer forms the very small sub-micron features necessary to reach current device densities. But these sub-micron features are difficult to analyze for characteristics such as their composition or thickness using standard spectroscopy techniques. These systems themselves and the excitation beam spots require certain minimal area to operate accurately and effectively—areas larger than the sub-micron IC feature sizes.

Figure 1:
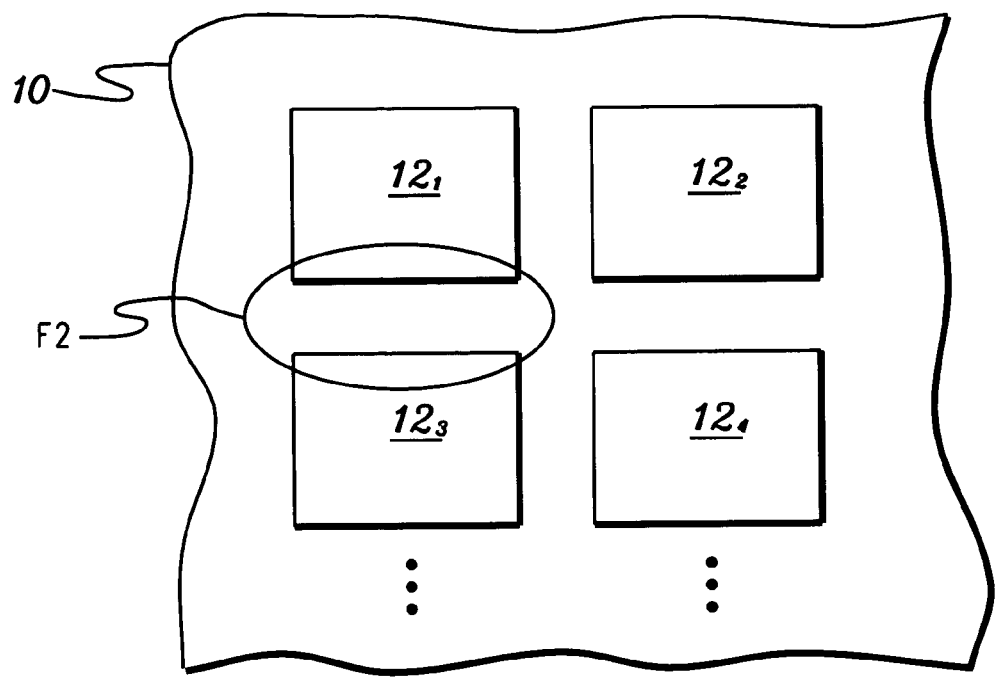
FIG. 1 depicts a portion of an integrated circuit (IC) wafer having several chip regions.
Figure 2:
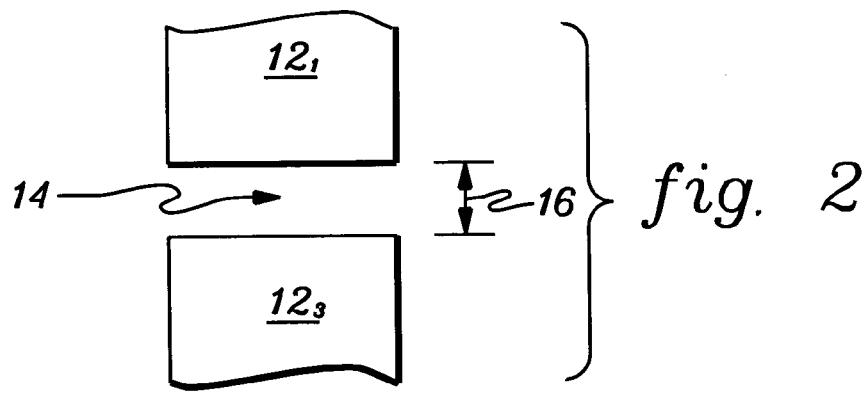
FIG. 2 depicts a scribe-line region between two chip regions.
Figure 3:
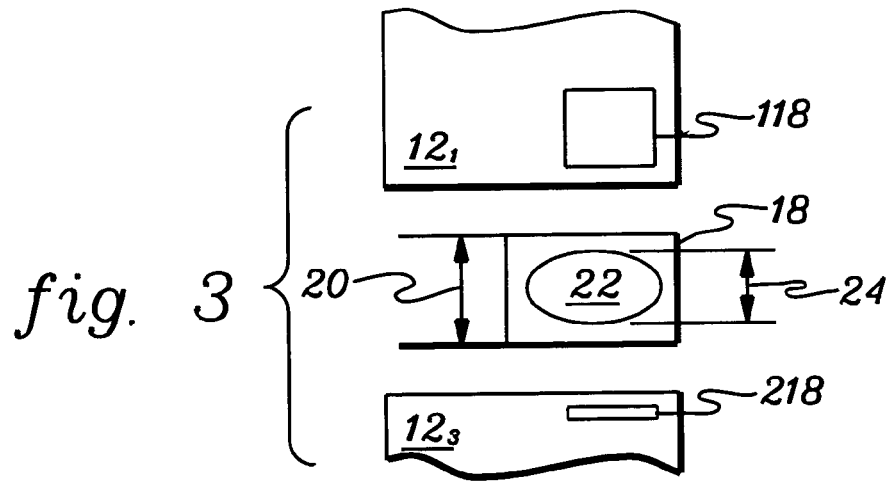
FIG. 3 depicts a test pattern of a film deposited in the scribe-line region, and other test regions in the chip regions themselves.

One technique involves exploiting some of the open, larger areas on the wafer, outside of the chip regions. For example, and with reference to FIGS. 1–3, wafer 10 usually includes an array of spaced chip regions $12_1 \ldots 12_4$, which will ultimately be diced into individual chips. FIG. 2 depicts the "scribe line" area 14 between two chip regions $12_1$ and $12_3$. The spacing 16 between the chip regions $12_1$ and $12_3$ is adequately sized to allow dicing of the wafer into individual chips along the scribe line area. Spacing 16 is, in one embodiment, <100 microns. The scribe line area can be used for the deposition of larger areas of a sample material (e.g., specialty conductive films Ta and Ti used in chip interconnects). For example, FIG. 3 shows an embodiment of a sample area 18 (of width 20—e.g., <70 microns) and having an "ideal" spectroscopy spot size 22 (of width 24—e.g., <50 microns) falling fully within the sample area. As discussed above, when analyzing a particular material (i.e., the thickness of a deposited specialty film) it is important to ensure that this spot size is fully within the sample material area to assure a consistent coverage ratio—when compared to the calibrated data—for reliable analysis results. Unused areas in the chip regions themselves (i.e., 118 and 218) can also be used for the deposition of larger sample areas of materials for testing and also fall within the scope of the invention for ICs.

To confine the excitation beam to the sample area, prevent unnecessary scattering, and prevent emissions from areas outside of the sample area reaching the detector, the present invention provides a mask having an elongate aperture sized according to the sample area widths, and also compatible with the fundamental beam excitation and detection path requirements of x-ray analysis systems.

Figure 4:
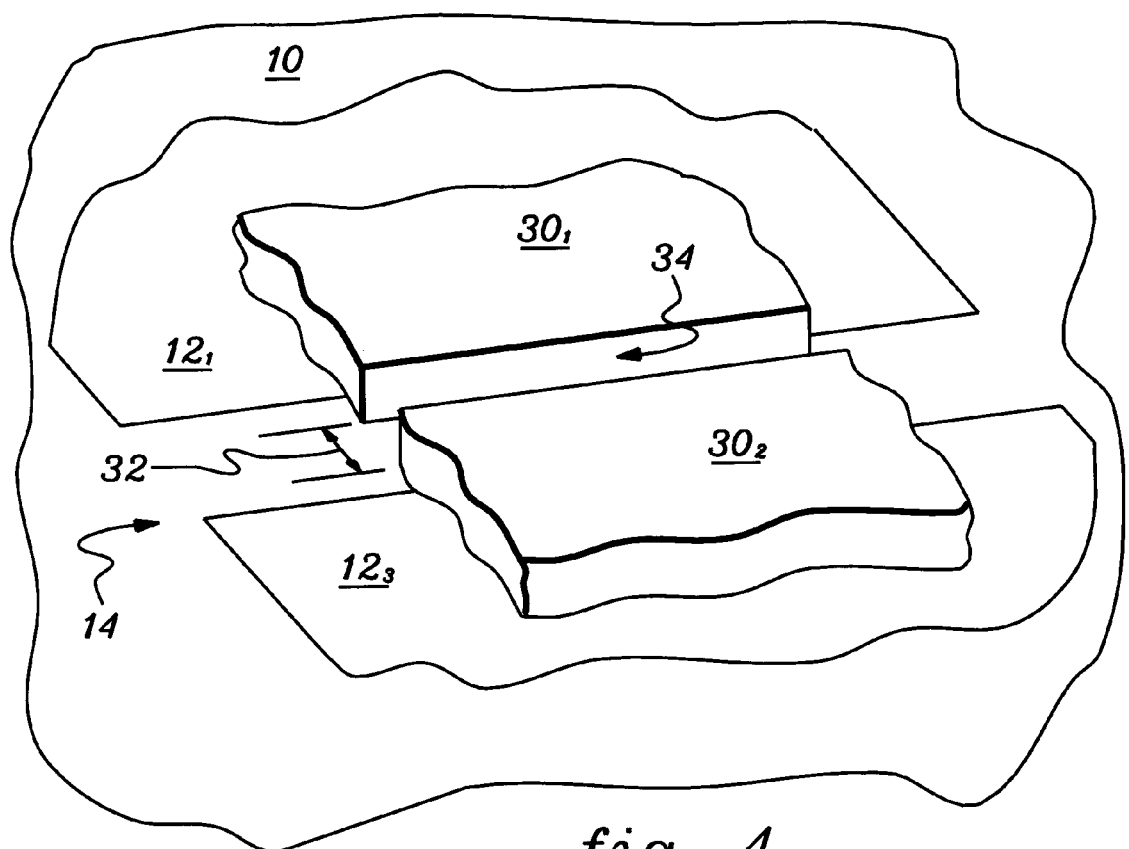
FIG. 4 is a perspective view of a portion of a spectroscopy system of the present invention showing a moveable mask with an elongated aperture shaped according to the test pattern in the scribe line.
Figure 5:
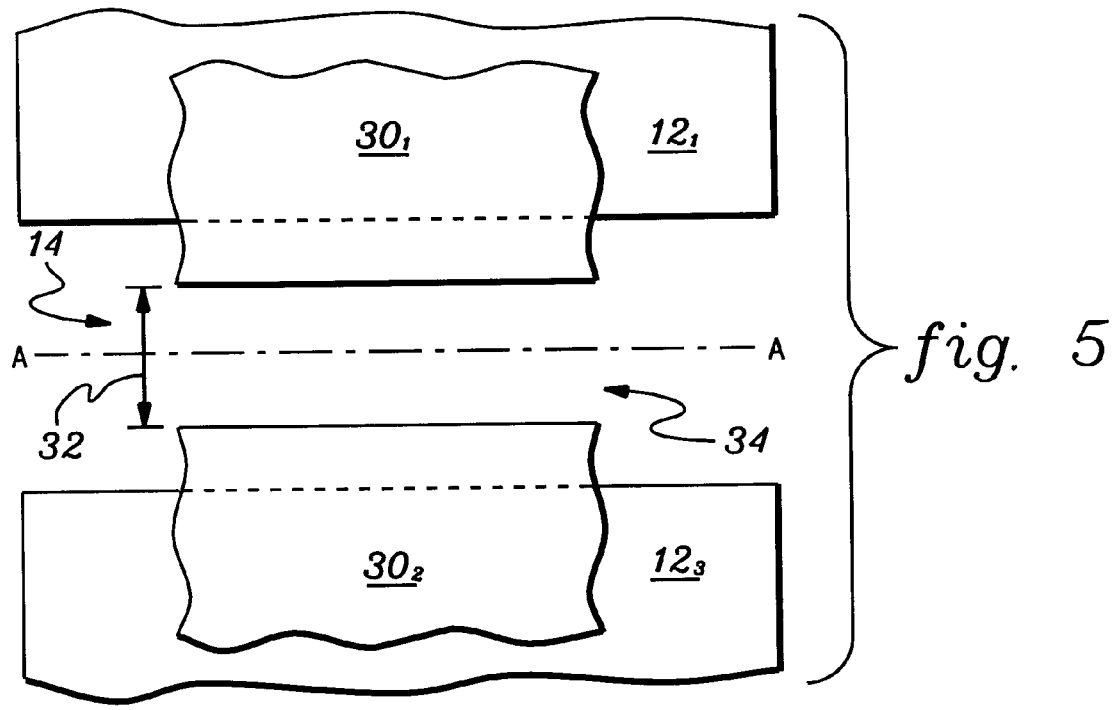
FIG. 5 is a top view of the portion of the system of FIG. 4.

For example, and with reference to the perspective view of FIG. 4 and the top view of FIG. 5, mask 30 formed of opposing sections $30_1$ and $30_2$ includes an elongate aperture 34. This mask blocks and confines the radiation in both the excitation and emission paths to a planar, elongate radiation path, parallel to the axis of the aperture. When the aperture is placed above the underlying sample area, over the scribe line 14 (and parallel to the axis A—A of the scribe line), the utility and performance of an analysis system can be greatly enhanced for IC fabrication. Measuring a characteristic in this scribe line region (e.g., film thickness) can be a valuable and accurate predictor of the thickness of the highly patterned features in the chip region.

Aperture spacing 32, for the examples noted above, should be <50 microns to ensure that the excitation beam falls fully within the width of the sample area. Moreover, this aperture width prevents emissions from materials outside of the sample area from reaching the detector. The elongate aperture preserves the integrity of the excitation and emission paths along the narrow elongate path, parallel to its axis.

The mask can be fixed itself (e.g., a contact mask placed directly on the patterned surface) or moveable relative to the surface along with the instrument, as discussed in greater detail below. If moveable, the spacing between the mask and sample in IC applications may be less that 100 microns, possibly 10–20 microns.

FIG. 6a depicts one embodiment of an XRF instrument 60, which includes the mask 30, in accordance with the present invention. The entire instrument, including mask 30, can be moved relative to the underlying IC wafer 10, and can therefore analyze multiple test areas in multiple scribe lines across the wafer. The instrument includes a source 40, detector 50, and beam controlling optic 70. The source, detector, optic and mask define the radiation path formed by the excitation and emission radiation. FIG. 6a shows the instrument with the source/optic arranged perpendicular to the wafer 10. FIG. 6b shows instrument 60 with the source/optic arranged at an angle to the wafer. This configuration leaves additional room for another device 80. Mask 30 allows these shallower excitation angles (because of its elongate shape), and also allows the source/optic combination to be placed at a greater distance from the sample area—resulting in this extra space for additional devices. Alternatively, the detector can be placed closer to the sample area.

Figure 7A:
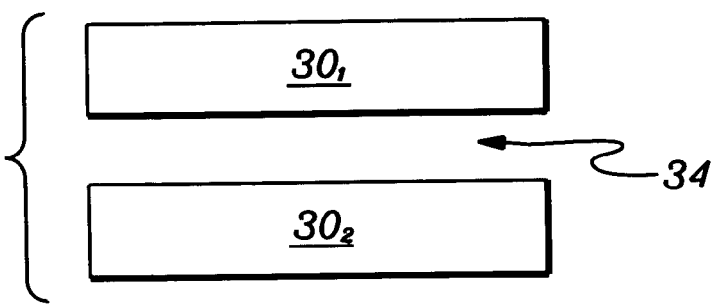
FIGS. 7a–e depict alternate, exemplary embodiments of the mask with an elongated aperture, in accordance with the present invention.
Figure 7B:
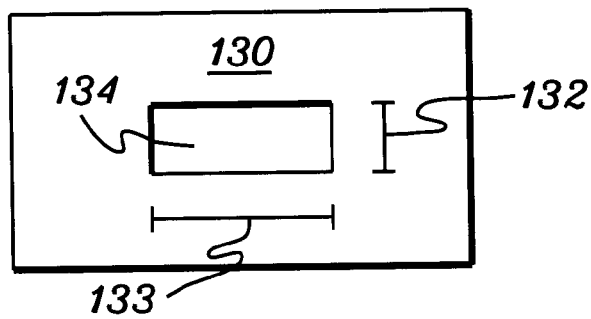
Figure 7C:
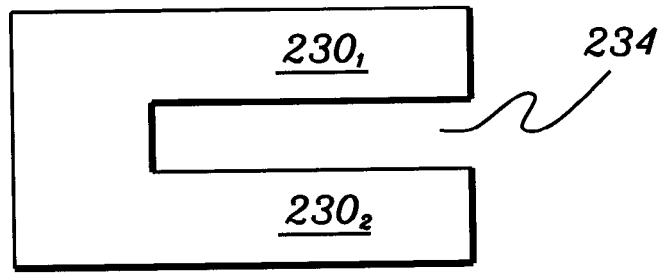
Figure 7D:
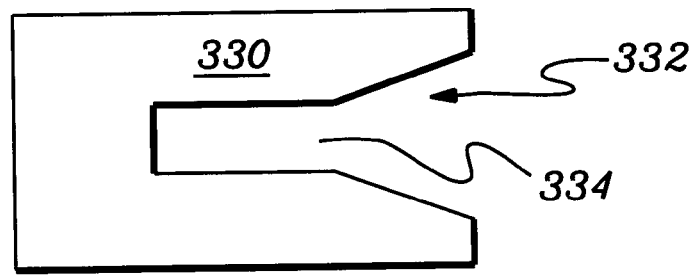
Figure 7E:
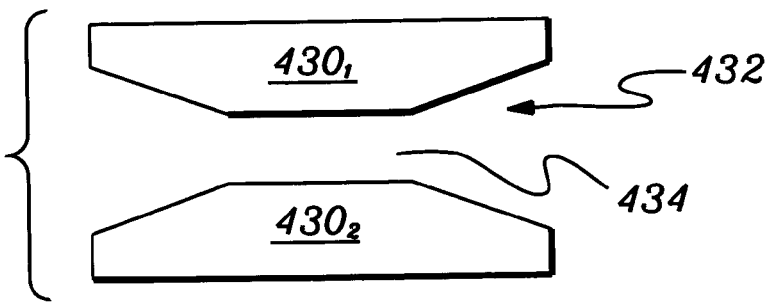

FIGS. 7a–e depict alternate embodiments of the mask of the present invention: The mask of FIG. 7a shows two opposing sections $30_1$ and $30_2$ forming the elongate aperture 34. These sections may be separately mounted and aligned using other structures. The mask of FIG. 7b shows a unitary structure 130 having an elongate, rectangular aperture 134 with shorter and longer sides, 132 and 133, respectively. The mask of FIG. 7c (used as a further example below) also shows a unitary structure with two arms $230_1$ and $230_2$ having the elongate aperture 234 open on one side. The mask of FIG. 7d shows a similar unitary structure 330, with an angled profile 332 partially forming the elongate aperture 334. Finally, the mask of FIG. 7e shows separate sections $430_1$ and $430_2$ each having angled profiles 432 forming a portion of elongate aperture 434.

Non-elongate versions of the aperture are also within the scope of the present invention, however, are less likely to be of significant importance. The elongate masks disclosed above maintain the integrity of the excitation and emission radiation paths, which necessarily combine into an elongate path with their relatively low angles of incidence. If the incidence angles of both paths increase (so that the angle between them decreases toward full parallelism), then the path formed may be less elongate and could be managed with apertures such as squares or circles. This is a possible, though unlikely scenario given the distance and efficiency concerns that would arise.

The material forming the mask and its thickness can be determined by one of ordinary skill in the art according to instrument design principles. For example, the material should be of a proper composition and thickness to perform the confinement and blocking functions. The mask should also not emit in response to the incident energy. Other exemplary requirements for the mask material(s):

1) The material should not emit strong X-ray fluorescence.
2) The material should not contain important analyte.
3) The material should stop X-rays, while remaining relatively thin.
4) The material should not scatter X-rays.

Example: For Mo—K excitation, single metal layers of Zr, Nb, Mo, Ru, Rh, Pd, Ag, In, Sn are appropriate. However, overlaps between the L-lines of the element and lines of analyte should be considered. For example, to stop 99.9% Mo—K, the thickness of an Mo sheet should be 0.33 mm. To reduce the total thickness, multi-layer construction may be used, having an inner layer primarily for stopping X-rays, of Ta, W, Re, Ir, Pt, Au, or Pb. For example, to stop 99.9% Mo—K, the thickness of an inner Au layer should be 0.047 mm. The outer layer is primarily for stopping X-ray fluorescence emitted by the inside material for which Zr, Nb, Mo, Ru, Rh, Pd, Ag, In, and Sn are appropriate. For example, to stop 99.9% Pb-L, the thickness of an outer Mo film should be 0.007 mm.

The optics discussed above used for controlling the excitation and/or emitted radiation can be of any suitable type including monocapillary optics (see, e.g., X-Ray Optical Systems, Inc. U.S. Pat. No. 5,747,821 all of which is incorporated by reference herein in its entirety); polycapillary optics (see, e.g., X-Ray Optical Systems, Inc. U.S. Pat. Nos. 5,192,869; 5,175,755; 5,497,008; 5,745,547; 5,570,408; and 5,604,353;—all of which are incorporated by reference herein in their entirety); curved crystal optics (see e.g., X-Ray Optical, Inc. U.S. Pat. Nos. 6,285,506 and 6,317,483 all of which are incorporated by reference herein in their entirety); multi-layer optics and pin-hole or slot collimating optics. The optics may provide beam gain, as well as general beam control.

Also, as discussed above, monochromating optical elements may be desirable in the excitation and/or emission paths for narrowing the radiation bands depending on the sample material's characteristic signatures. Many of the optics discussed above, especially curved crystal optics and multi-layer optics, can be employed for this function, as set forth in many of the above-incorporated U.S. patents.

Optic/source combinations are also useable such as those disclosed in X-Ray Optical Systems, Inc. U.S. Provisional Application Ser. Nos. 60/398,968 (filed Jul. 26, 2002 entitled METHOD AND DEVICE FOR COOLING AND ELECTRICALLY-INSULATING A HIGH-VOLTAGE, HEAT-GENERATING COMPONENT, and perfected as PCT Application PCT/US02/38803) and 60/398,965 (filed Jul. 26, 2002 entitled X-RAY SOURCE ASSEMBLY HAVING ENHANCED OUTPUT STABILITY, and perfected as PCT Application PCT/US02/38493)—all of which are incorporated by reference herein in their entirety.

Figure 8A:
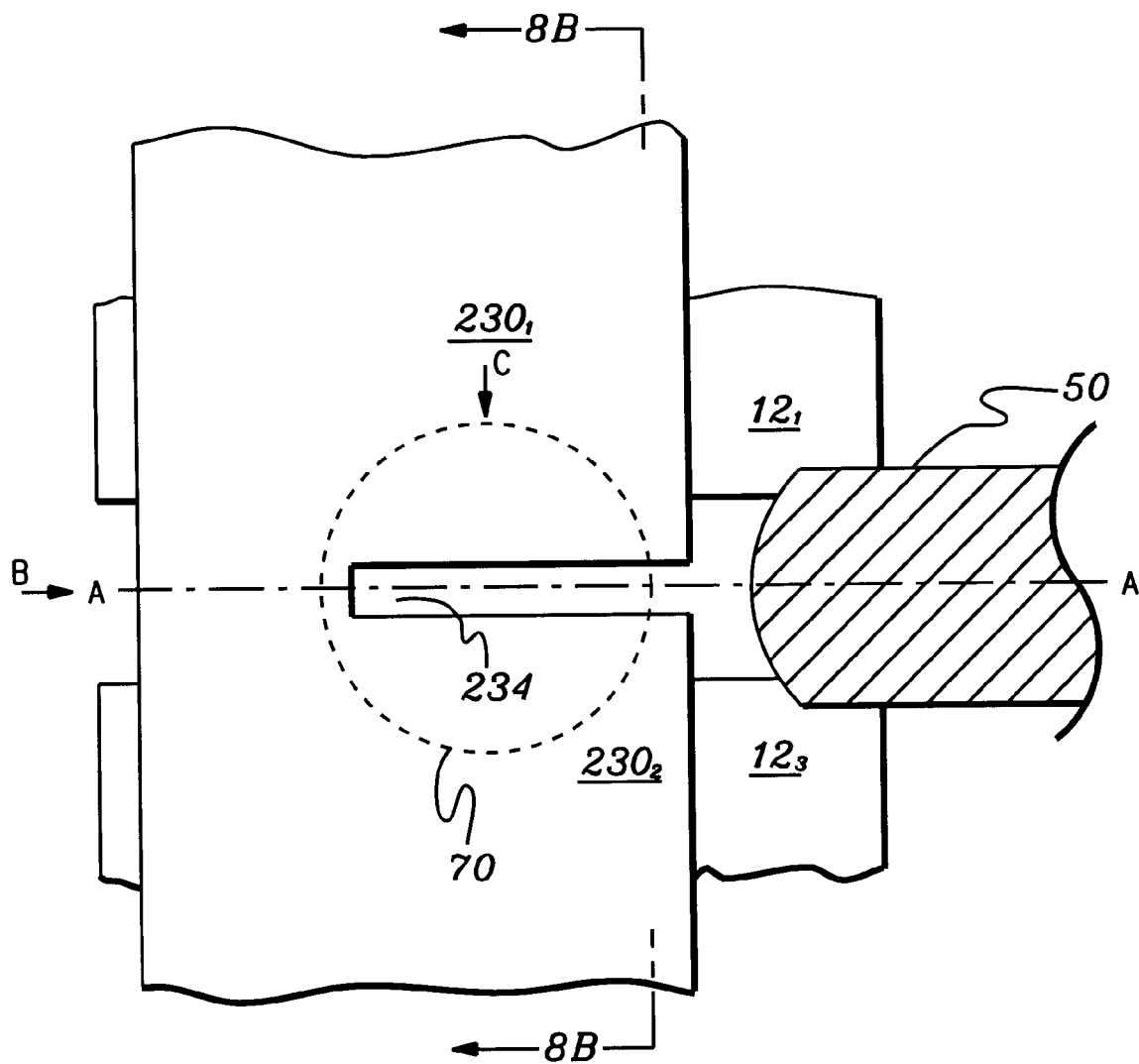
FIGS. 8a–c are top, side sectional and perspective views, respectively, of a portion of the spectroscopy system of FIG. 6a showing alignment of the source, aperture and detector along axis A—A.
Figure 8B:
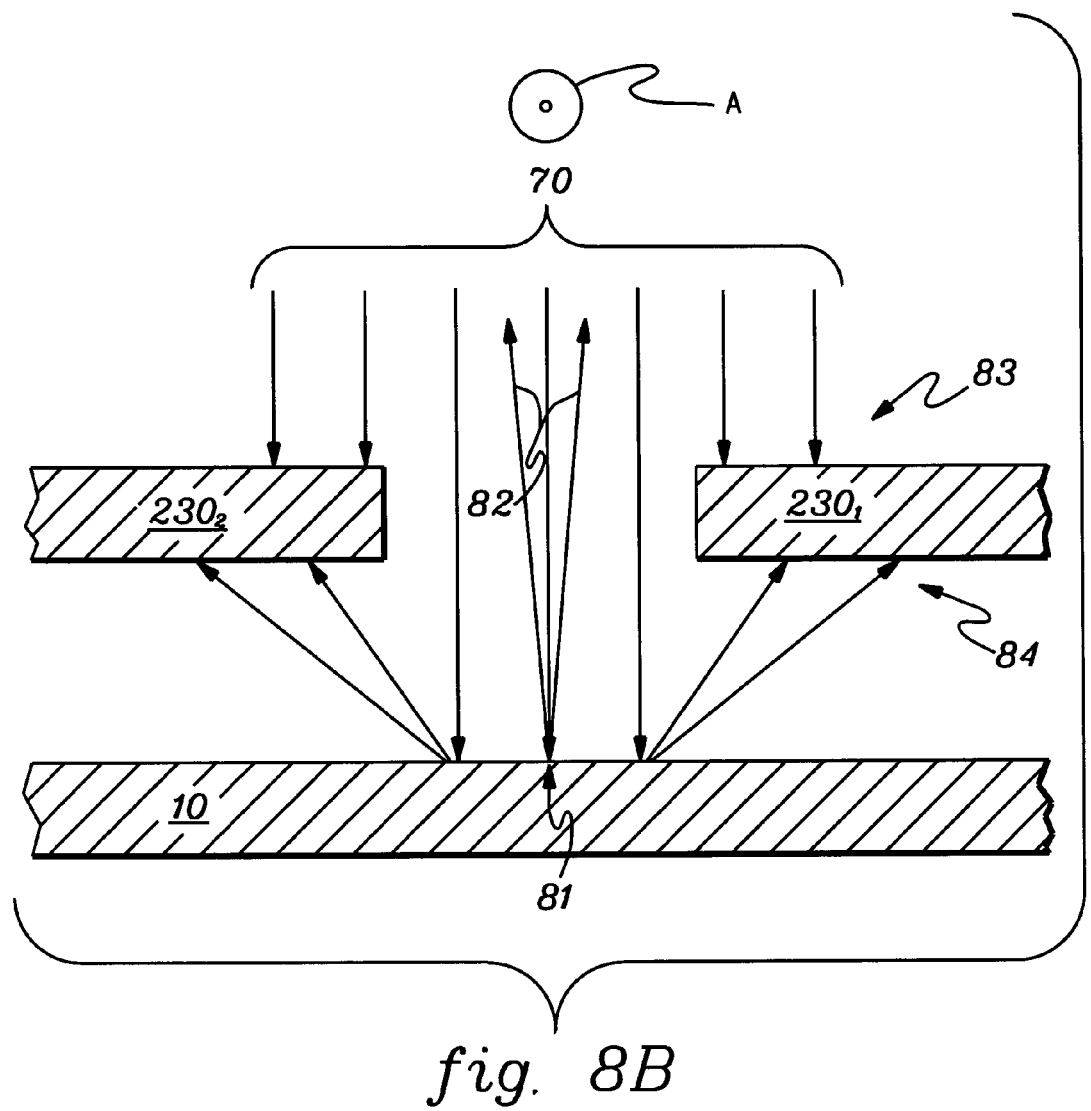

FIG. 8a is a top, sectional view of the instrument of FIG. 6a, showing the alignment of optic 70, aperture 234 of mask $230_1/230_2$ with detector 50 in a generally planar radiation path parallel to axis A—A. Operating along this elongate axis confines the excitation radiation to the scribe line sample area between chip regions $12_1$ and $12_3$; and also ensures that all emissions toward detector 50 are limited to emissions only from the sample area, and that any stray emissions are blocked. The side, sectional view of FIG. 8b offers additional detail of this confinement/blocking function of mask sections $230_1$ and $230_2$. The upper surfaces confine the incident radiation by blocking rays 83; and the lower surfaces block any scattered rays 84, and ensure that only rays incident on the area 81 directly below the aperture 234 contribute to the fluorescence 82 from the wafer surface back to the detector (not shown).

Figure 8C:
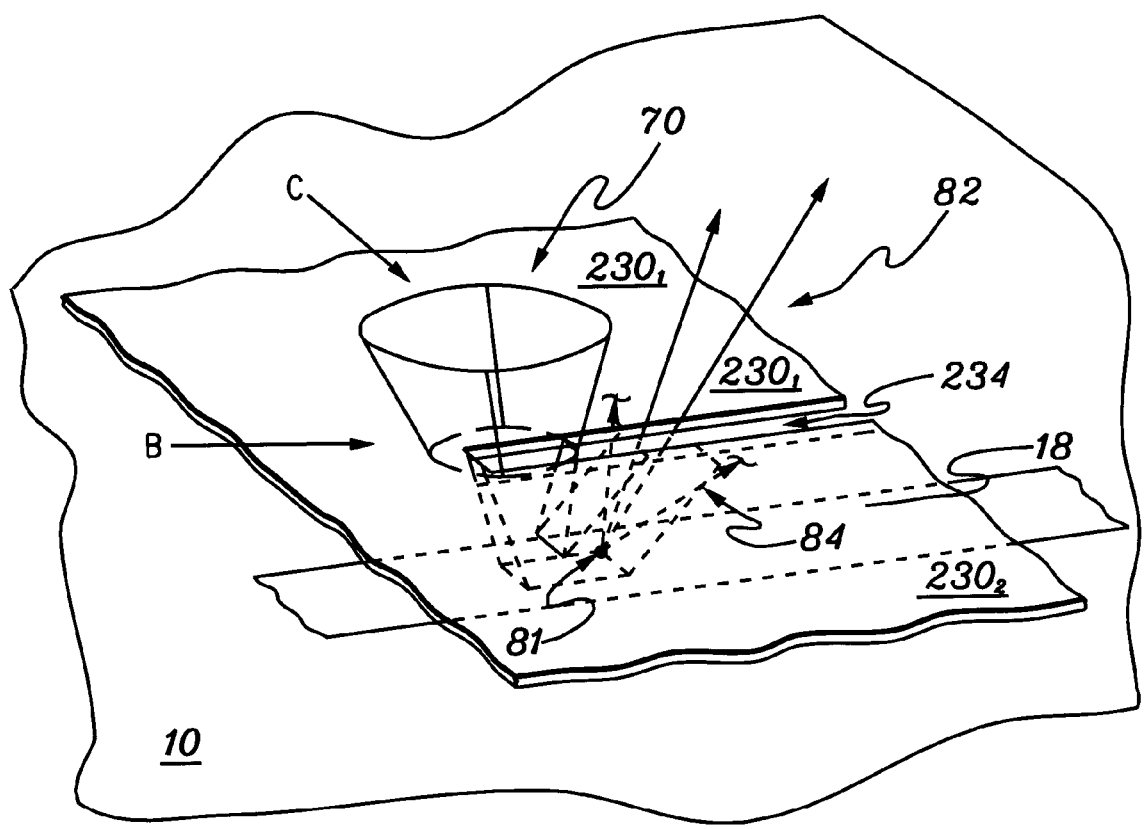

FIG. 8c is a perspective view of this instrument showing the confinement/blocking function on the incident beam, and also showing how only the desired fluorescence 82 is allowed toward the detector, with certain rays 84 blocked.

Expanding on the concepts disclosed in FIGS. 8a–c, FIG. 9 shows the beam profiles from directions B and C (shown in FIGS. 8a and 8c). The shaded areas 92 and 94 of the B profile are blocked by the mask, and the shaded area 96 of profile C is also blocked. The residual tail 98 is allowed into the propagation path along axis A—A as discussed above.

The invention disclosed herein extends to any sample analysis technique, where the profile of the sample area can be determined with some specificity. Its value to the semiconductor industry in particular lies in its ability to operate repeatedly within the larger scribe line areas between different chip regions on a single wafer, without requiring the sub-micron beam precision necessary to operate within the chip regions themselves. The use of the term "relative" when referring to any movement between the mask and the sample area is broad enough to include movement of one structure relative to the other, regardless of which is moving.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An apparatus for examining a region of a patterned surface, comprising:

a source for directing excitation x-ray, neutron, particle-beam or gamma ray radiation toward a two-dimensional sample area in the region of the surface;

a detector for detecting emissions emitted from the sample area; and a mask positioned in a planar radiation path formed by the source, detector and the sample area, and moveable relative to the sample area, the moveable mask including an elongate aperture to substantially confine the excitation radiation directed to the sample area, and the emissions from the sample area, to the planar radiation path when arranged parallel to a first axis of the two-dimensional sample area.

2. The apparatus of claim 1, wherein the source, detector and mask are separate from the patterned surface and together moveable relative to the patterned surface.

3. The apparatus of claim 1, wherein the source and detector are aligned along the longitudinal axis of the elongate aperture in the planar radiation path.

4. The apparatus of claim 1, further comprising an optical element for directing the excitation radiation from the source, through the elongate aperture, and toward the two-dimensional sample area of the patterned surface; and/or an optical element for directing the emissions from the aperture to the detector.

5. The apparatus of claim 4, wherein the optical element comprises a monocapillary element, a polycapillary element, a curved crystal element, a multi-layer element, a pin-hole element or a slot element.

6. The apparatus of claim 1, wherein the excitation radiation is substantially monochromatic in a radiation band characteristic of a sample material in the sample area.

7. The apparatus of claim 6, further comprising at least one monochromating optical element for monochromatizing the excitation radiation.

8. The apparatus of claim 1, wherein the width of the elongate aperture is sized according to the dimension of the sample area measured along a second axis perpendicular to the first axis of the sample area.

9. The apparatus of claim 1, further comprising an integrated circuit, wherein the region of the patterned surface comprises a test region within, between, or adjacent to, chip regions of the integrated circuit (IC), the test region including the sample area, the sample area having a substantially uniform layer of sample material therein, and wherein:

the movable mask substantially confines the excitation radiation to the sample area along the first axis, and the moveable mask substantially blocks emissions from the sample area other than those directed toward the detector, and substantially blocks emissions from areas other than the sample area, thereby allowing only emissions from the sample area along the first axis to be detected by the detector.

10. The apparatus of claim 9, wherein the substantially uniform layer of sample material in the sample area corresponds to material used for substantially smaller features in the chip regions of the IC.

11. The apparatus of claim 1, further comprising an integrated circuit (IC), wherein the region comprises a scribe-line region between chip regions of the integrated circuit (IC), the scribe-line region including the sample area, the sample area having a substantially uniform layer of sample material therein, and wherein the substantially uniform layer of sample material in the sample area corresponds to material used for substantially smaller features in the chip regions of the IC.

12. The apparatus of claim 1, wherein the radiation is x-rays, and the emissions are x-ray fluorescence emissions.

13. A method for examining a region of a patterned surface, comprising:
directing excitation x-ray, neutron, particle-beam or gamma ray radiation toward a two-dimensional sample area in the region of the patterned surface;
detecting emissions emitted from the sample area; and
positioning a mask in a planar radiation path formed by the source, detector and the sample area, and moveable relative to the sample area, the moveable mask including an elongate aperture to substantially confine the excitation radiation directed to the sample area, and the emissions from the sample area, to the planar radiation path when arranged parallel to a first axis of the two-dimensional sample area.

14. The method of claim 13, further comprising
moving the moveable mask, source, and detector relative to the sample area of the patterned surface.

15. The method of claim 13, wherein the source and detector are aligned along the longitudinal axis of the elongate aperture in the planar radiation path.

16. The method of claim 13, further comprising:
using an optical element for directing the excitation radiation from the source, through the elongate aperture, and toward the two-dimensional sample area of the patterned surface; and/or an optical element for directing the emissions from the aperture to the detector.

17. The method of claim 16, wherein the optical element comprises a monocapillary element, a polycapillary element, a curved crystal element, a multi-layer element, a pin-hole element or a slot element.

18. The method of claim 13, further comprising:
monochromatizing the excitation radiation wherein the excitation radiation is substantially monochromatic in a radiation band characteristic of a sample material in the sample area.

19. The method of claim 13, wherein the width of the elongate aperture is sized according to the dimension of the sample area measured along a second axis perpendicular to the first axis of the sample area.

20. The method of claim 13, wherein the region comprises a test region within, between, or adjacent to, chip regions of an integrated circuit (IC), the test region including the sample area, the sample area having a substantially uniform layer of sample material therein, and wherein:
the movable mask substantially confines the excitation radiation to the sample area along the first axis, and
the moveable mask substantially blocks emissions from the sample area other than those directed toward the detector, and substantially blocks emissions from areas other than the sample area, thereby allowing only emissions from the sample area along the first axis to be detected by the detector.

21. The method of claim 20, wherein the substantially uniform layer of sample material in the sample area corresponds to material used for substantially smaller features in the chip regions of the IC.

22. The method of claim 13, wherein the region comprises a scribe-line region between chip regions of an integrated circuit (IC), the scribe-line region including the sample area, the sample area having a substantially uniform layer of sample material therein, and wherein the substantially uniform layer of sample material in the sample area corresponds to material used for substantially smaller features in the chip regions of the IC.

23. The method of claim 13, wherein the radiation is x-rays, and the emissions are x-ray fluorescence emissions.

24. An apparatus for examining a region of a patterned surface, comprising:
a source for directing excitation x-ray, neutron, particle-beam or gamma ray radiation toward a two-dimensional sample area in the region of the surface;
a beam controlling optical element for directing the excitation radiation from the source toward the surface;
a detector for detecting emissions emitted from the sample area; and
a mask positioned in a planar radiation path formed by the source, detector and the sample area, the mask including an elongate aperture to substantially confine the excitation radiation directed to the sample area, and the emissions from the sample area, to the planar radiation path when arranged parallel to a first axis of the two-dimensional sample area.

25. The apparatus of claim 24, wherein the mask is a contact mask on the sample area, and the source and detector are separate from the patterned surface and together moveable relative to the patterned surface.

26. The apparatus of claim 24, wherein the source and detector are aligned along the longitudinal axis of the elongate aperture in the planar radiation path.

27. The apparatus of claim 24, wherein the optical element comprises a gain-providing optic.

28. The apparatus of claim 24, wherein the optical element comprises a monocapillary element, a polycapillary element, a curved crystal element, a multi-layer element, a pin-hole element or a slot element.

29. The apparatus of claim 24, wherein the excitation radiation is substantially monochromatic in a radiation band characteristic of a sample material in the sample area.

30. The apparatus of claim 29, further comprising at least one monochromating optical element for monochromatizing the excitation radiation.

31. The apparatus of claim 24, wherein the width of the elongate aperture is sized according to the dimension of the sample area measured along a second axis perpendicular to the first axis of the sample area.

32. The apparatus of claim 24, further comprising an integrated circuit (IC), wherein the region of the patterned surface comprises a test region within, between, or adjacent to, chip regions of the integrated circuit (IC), the test region including the sample area, the sample area having a substantially uniform layer of sample material therein, and wherein:
the mask substantially confines the excitation radiation to the sample area along the first axis.

33. The apparatus of claim 32, wherein the substantially uniform layer of sample material in the sample area corresponds to material used for substantially smaller features in the chip regions of the IC.

34. The apparatus of claim 24, further comprising an integrated circuit (IC), wherein the region comprises a scribe-line region between chip regions of the integrated circuit (IC), the scribe-line region including the sample area, the sample area having a substantially uniform layer of sample material therein, and wherein the substantially uniform layer of sample material in the sample area corresponds to material used for substantially smaller features in the chip regions of the IC.

35. The apparatus of claim 24, wherein the radiation is x-rays, and the emissions are x-ray fluorescence emissions.

36. A method for examining a region of a patterned surface, comprising:

directing excitation x-ray, neutron, particle-beam or gamma ray radiation toward a two-dimensional sample area in the region of the patterned surface using a beam controlling optical element;

detecting emissions emitted from the sample area; and positioning a mask in a planar radiation path formed by the source, detector and the sample area, the mask including an elongate aperture to substantially confine the excitation radiation directed to the sample area, and the emissions from the sample area, to the planar radiation path when arranged parallel to a first axis of the two-dimensional sample area.

37. The method of claim 36, wherein the mask is a contact mask over the sample area, the method further comprising:

moving the source and detector relative to sample area of the patterned surface.

38. The method of claim 36, wherein the source and detector are aligned along the longitudinal axis of the elongate aperture in the planar radiation path.

39. The method of claim 36, wherein the optical element comprises a gain-providing optical element.

40. The method of claim 36, wherein the optical element comprises a monocapillary element, a polycapillary element, a curved crystal element, a multi-layer element, a pin-hole element or a slot element.

41. The method of claim 36, further comprising:

monochromatizing the excitation radiation wherein the excitation radiation are substantially monochromatic in a radiation band characteristic of a sample material in the sample area.

42. The method of claim 36, wherein the width of the elongate aperture is sized according to the dimension of the sample area measured along a second axis perpendicular to the first axis of the sample area.

43. The method of claim 36, wherein the region comprises a test region within, between, or adjacent to, chip regions of an integrated circuit (IC), the test region including the sample area, the sample area having a substantially uniform layer of sample material therein, and wherein:

the mask substantially confines the excitation radiation to the sample area along the first axis.

44. The method of claim 43, wherein the substantially uniform layer of sample material in the sample area corresponds to material used for substantially smaller features in the chip regions of the IC.

45. The method of claim 36, wherein the region comprises a scribe-line region between chip regions of an integrated circuit (IC), the scribe-line region including the sample area, the sample area having a substantially uniform layer of sample material therein, and wherein the substantially uniform layer of sample material in the sample area corresponds to material used for substantially smaller features in the chip regions of the IC.

46. The method of claim 36, wherein the radiation is x-rays, and the emissions are x-ray fluorescence emissions.

* * * * *

UNITED STATES PATENT AND TRADEMARK OFFICE
CERTIFICATE OF CORRECTION

| | | |
|---|---|---|
| PATENT NO. | : 7,023,955 B2 | Page 1 of 1 |
| APPLICATION NO. | : 10/639359 | |
| DATED | : April 4, 2006 | |
| INVENTOR(S) | : Chen et al. | |

It is certified that error appears in the above-identified patent and that said Letters Patent is hereby corrected as shown below:

Title Page:

(73) Assignee:

Insert --and TECHNOS Co., Ltd., Osaka, JAPAN-- after "X-Ray Optical System, Inc., East Greenbush, NY (US)"

Signed and Sealed this

Fourth Day of September, 2007

JON W. DUDAS
*Director of the United States Patent and Trademark Office*